United States Patent
Kwiatkowski et al.

(10) Patent No.: US 6,689,791 B2
(45) Date of Patent: Feb. 10, 2004

(54) CARBOXYLATED HETEROCYCLIC COMPOUNDS AND METHODS OF SYNTHESIS

(75) Inventors: Stefan Kwiatkowski, Lexington, KY (US); Miroslaw Golinski, Lexington, KY (US)

(73) Assignee: R. T. Alamo Ventures I, LLC, Beverly Hills, CA (US)

( * ) Notice: Subject to any disclaimer, the term of this patent is extended or adjusted under 35 U.S.C. 154(b) by 0 days.

(21) Appl. No.: 10/281,800

(22) Filed: Oct. 28, 2002

(65) Prior Publication Data

US 2003/0166678 A1 Sep. 4, 2003

Related U.S. Application Data

(60) Provisional application No. 60/360,829, filed on Mar. 1, 2002.

(51) Int. Cl.$^7$ .................. A61K 31/47; C07D 215/36
(52) U.S. Cl. ..................................... 514/312; 546/155
(58) Field of Search .......................... 546/155; 514/318

(56) References Cited

U.S. PATENT DOCUMENTS 6,307,050 B1 * 10/2001 Kwiatowski et al. ....... 546/155

* cited by examiner

*Primary Examiner*—Patricia L. Morris
(74) *Attorney, Agent, or Firm*—Medlen & Carroll, LLP

(57) ABSTRACT

Compositions of the present invention comprise carboxylated heterocyclic compounds, including carboxyflosequinan. The methods of the present invention also comprise the synthesis of carboxyflosequinan.

11 Claims, 3 Drawing Sheets

| CAT. # | TARGET | BATCH*SPP. | n= | CONC. | †% INHIBITION % -100 -50 0 50 100 | | $IC_{30}$ | $K_1$ | $n_H$ | R |
|---|---|---|---|---|---|---|---|---|---|---|
| 178010 | PROTEIN SERINE/THREONINE KINASE PKC, NON-SELECTIVE | 45090 RAT | 2 | 1000 μM | 85 | | <100 μM | | | |
| ◆ | | | 2 | 300 μM | 71 | | | | | |
| ◆ | | | 2 | 100 μM | 53 | | | | | |
| ◆ | | | | | | | | | | |

*BATCH: REPRESENTS COMPOUNDS TESTED CONCURRENTLY IN THE SAME ASSAY(S).

◆ DENOTES ITEM MEETING THE CRITERIA FOR SIGNIFICANCE

†RESULTS WITH ≥ 50% STIMULATION OR INHIBITION ARE BOLDFACED.
(NEGATIVE VALUES CORRESPOND TO STIMULATION OF BINDING OR ENZYME ACTIVITY)

R = ADDITIONAL COMMENTS

FIG. 3

CARBOXYLATED HETEROCYCLIC COMPOUNDS AND METHODS OF SYNTHESIS

"This application for patent under 35 U.S.C. 111(a) claims priority to Provisional Application Ser. No. 60/360,829 filed on Mar. 1, 2002 under 35 U.S.C. 111(b)."

FIELD OF THE INVENTION

The present invention teaches compositions comprising carboxylated heterocyclic compounds and the synthesis of the same.

BACKGROUND

A variety of heterocyclic compounds have been described as having various pharmaceutical applications. However, the synthesis of such compounds, especially on a large scale, is often labor-intensive, expensive and time consuming. What is needed therefore, is a simplified and economical method for the synthesis and purification of heterocyclic compounds.

SUMMARY OF THE INVENTION

The present invention relates to compositions comprising carboxyflosequinan and the synthesis of the same.

In one embodiment, the present invention teaches a carboxylated heterocyclic compound corresponding to 3-carboxymethylsulfinyl-7-fluoro-1-methyl-4-quinolone (carboxyflosequinan) and derivatives thereof.

In one embodiment, the present invention teaches providing, 3-cyanomethylthio-7-fluoro-1-methyl-4-quinolone and a first acid followed by the reaction of said 3-cyanomethylthio-7-fluoro-1-methyl-4-quinolone and first acid under conditions such that 3-carboxymethylthio-7-fluoro-1-methyl-4-quinolone is produced.

In another embodiment the present invention further contemplates the reaction of 3-carboxymethylthio-7-fluoro-1-methyl-4-quinolone with a second acid and a peroxide under conditions such that 3-Carboxymethylsulfinyl-7-fluoro-1- methyl-4-quinolone is produced.

DESCRIPTION OF THE DRAWINGS

FIG. 3 depicts the results of enzyme (PKC) inhibition assays with 3-carboxymethylsulfinyl-7-fluoro-1-methyl-4-quinolone.

DEFINITIONS

Figure 1:
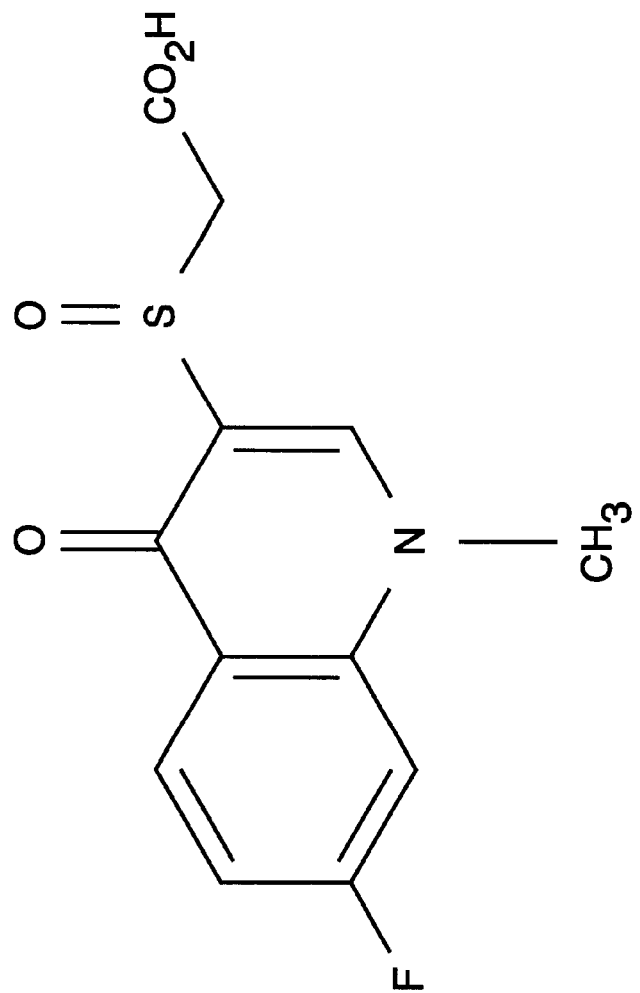
FIG. 1 shows the chemical structure of 3-carboxymethylsulfinyl-7-fluoro-1-methyl-4-quinolone.
Figure 2:
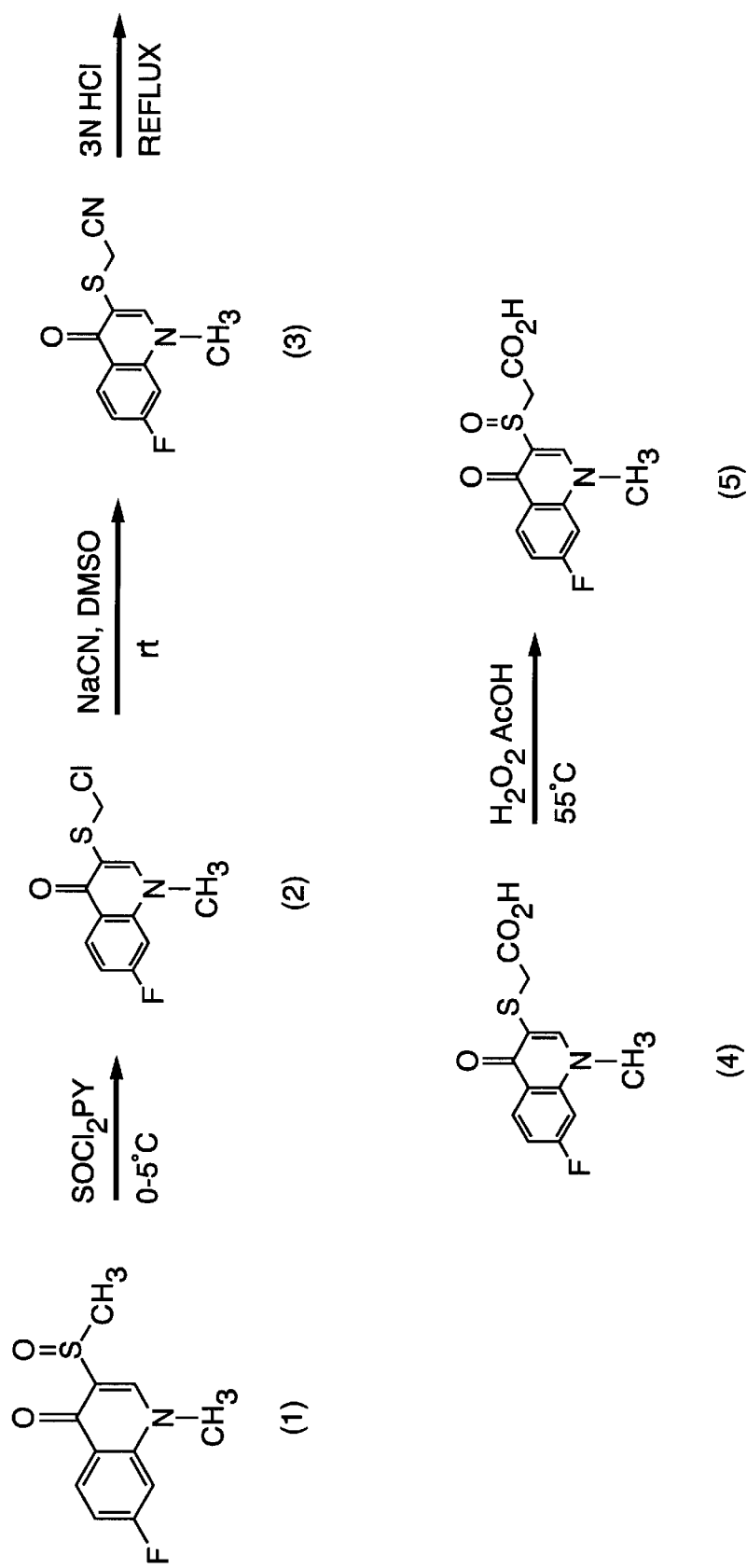
FIG. 2 displays a scheme for the synthesis of 3-carboxymethylsulfinyl-7-fluoro-1-methyl-4-quinolone.

As used herein carboxyflosequinan refers to the chemical composition designated as 3-carboxymethylsufinyl-7-fluoro-3-methyl-4-quinolone having the chemical structure corresponding to:

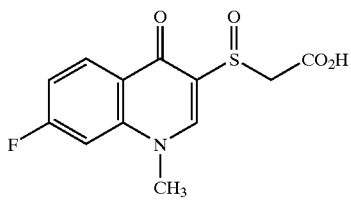

As used herein, the phrase "flosequinan" and a "a racemic mixture of flosequinan" refers to 7-fluoro-1-methyl-3-(methylsulphinyl)-4(1H)-quinolinone which may also be described as 7-fluoro-1-methyl-3-(methylsulfinyl)-4(1H)-quinolone) and as 7-fluoro-1-methyl-3-methylsulfinyl-4-quinolone having the chemical structure of:

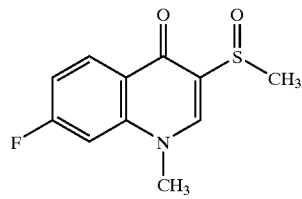

As used herein, "room temperature", "RT" or "ambient temperature" is approximately 18° C. to 25° C.

As used herein, "overnight" is approximately 8 hours, more preferably 12 hours, more typically 17 hours, but can be up to approximately 30 hours.

As used herein, a "heterocyclic" compound refers to a compound comprising a ring composed of atoms of more than one kind.

As used herein, a "catalyst" refers to a substance that, when added to a reaction mixture, changes (e.g. speeds up) the rate of attainment of equilibrium in the system without itself undergoing a permanent chemical change. Examples of suitable catalysts contemplated for use in the present invention include, but are not limited to, antimony chloride and carbon tetrabromide.

As used herein, a "solvent" refers to a substance that will dissolve other substances. An "organic solvent" is an organic substance that will dissolve other substances. Examples of solvents suitable for use in embodiments of the present invention include, but are not limited to dichloromethane and acetonitrile.

DETAILED DESCRIPTION OF THE INVENTION

In one embodiment, the present invention describes a composition comprising carboxyflosequinan. In another embodiment, the present invention teaches methods for the synthesis of carboxyflosequinan.

The present invention also contemplates the formulation of carboxyflosequinan as a pharmaceutically acceptable salt. In addition, pharmaceutical formulations of carboxyflosequinan may also contain binders, fillers, carriers, preservatives, stabilizing agents, emulsifiers, buffers and excipients as, for example, pharmaceutical grades of mannitol, lactose, starch, magnesium stearate, sodium saccharin, cellulose, and magnesium carbonate. The present invention also contemplates the administration of carboxyflosequinan as a pharmaceutically acceptable salt or formulation. The present invention also contemplates the administration of carboxyflosequinan and carboxyflosequinan formulations to a subject.

Methods of producing a racemic mixture of flosequinan, as set out in U.S. Pat. Nos. 5,079,264 and 5,011,931 to MacLean et al., are hereby incorporated by reference. In one embodiment, flosequinan is prepared according to the protocol set out in Example 2.

Without limiting the invention to any particular mechanism, carboxyflosequinan is an enzyme inhibitors. In a specific example, carboxyflosequinan inhibit protein kinase C (herein after PKC). This effect of carboxyflosequinan on enzyme activity, more particularly on PKC, has utility in therapeutics.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); tmol (micromoles); nmol (nanomoles); g (grams); mg (milligrams); L (liters); ml (milliliters); ° C. (degrees Centigrade).

All bracketed numbers [e.g. "(1)"] after the chemical name of a compound, refer to the corresponding chemical structure as designated by the same bracketed number in FIG. 1.

All NMR spectra were recorded using Varian-Gemini 300 MHz Spectrometer.

In Examples 1, unless otherwise stated, the source for the chemical reagents was Aldrich, Milwaukee, Wis., USA (unless a reagent was synthesized de novo, as described in the examples). Flosequinan was synthesized according to the protocol provided in Example 2, unless specified otherwise.

EXAMPLE 1

Synthesis of 3-Carboxymethylsulfinyl-7-fluoro-1-methyl-4-quinolone (5)

To an efficiently stirred and gently cooled with dry-ice acetone mixture of 12 ml of thionyl chloride ($SOCl_2$) and 3 ml of pyridine (Py) at $-3°$ C. was added flosequinan (3.59 g, 15 mmol) (1) in a few portions over a period of approximately 1 min. During that time cooling was applied to keep the temperature in the range 0–6° C. The mixture was stirred at 0° C. for 5 min, cooled to $-5°$ C. and poured as a thin stream into 350 ml of ice-water with efficient stirring. After 10 min stirring at 0° C. a solid was filtered off, washed with water, and dried over phosphorus pentoxide under high vacuum. Yield 2.82 g (74 %) of a crude product that was ~95% pure by $^1$H NMR. The crude product (3-Chloromethylthio-7-fluoro-1-methyl-4-quinolone) (2) was used in the next step without further purification.

To efficiently stirred suspension of sodium cyanide (490 mg, 10 mmol) in dry DMSO (15 ml) at room temperature under a $N_2$ atmosphere was added crude 3-chloromethylthio-7-fluoro-1-methyl-4-quinolone (1.031 g, 4 mmol) (2) in a few portions. The mixture was stirred for 1 h and poured into diluted $H_2SO_4$ with ice. The solid was filtered off. The filtrate was extracted twice with ethyl acetate, the combined extracts were dried over anhydrous $Na_2SO_4$ and concentrated. The residue was combined with the solid and was chromatographed on silica gel with hexane-ethyl acetate (gradient 2:1,1:1,1:2) to give 644 mg (65%) of the product as a brownish solid. The product (3-Cyanomethylthio-7-fluoro-1-methyl-4-quinolone; 575 mg) (3) was further purified by recrystallization from methanol to give 382 mg of brownish crystals.

A mixture of 3-cyanomethylthio-7-fluoro-1-methyl-4-quinolone (265 mg, 1.067 mmol) (3) and 3N hydrochloric acid (8ml) was refluxed under a $N_2$ atmosphere for 2.5 h. The hot mixture was diluted with water (1 ml) and allowed to cool to room temperature. A solid that precipitated was filtered off and dried under high vacuum. The yield of 3-Carboxymethylthio-7-fluoro-1-methyl-4-quinolone (4) was 270 mg (94.7%).

50% hydrogen peroxide (57ml, 33.6 mg, 0.988 mmol) was added to a solution of 3-carboxymethylthio-7-fluoro-1-methyl-4-quinolone (4) in acetic acid (3.6 ml) at 60° C. and the mixture was stirred at 55° C. for 4 h. The hot mixture was diluted with water (12ml) and cooled to 0° C. A white solid that precipitated was filtered off and dried under high vacuum. The yield of 3-Carboxymethylsulfinyl-7-fluoro-1-methyl-4-quinolone was 185 mg (72.7%) (5).

EXAMPLE 2

In this example flosequinan is prepared according to the following protocol:

A. Preparation of Flosequinan i. Step I

In a clean and dry 12 L glass reactor equipped with a back suction trap plus a NaOH (25%) trap at the outlet and a back suction trap in the inlet, 3.840 L of toluene were charged and cooled to $-45°$ C. using a dry ice-acetone bath. Using appropriate safety precautions, 832 g of phosgene were then passed through the cold toluene while stirring to prepare a 20% (wt/wt) solution. The addition of the phosgene took approximately 3.5 hours.

Separately, into a clean and dry 22 L glass reactor equipped with the above-described types of back suction traps, 399 g of starting material (formula 1):

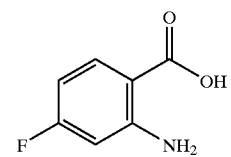

I was added with stirring to 4.37 L of deionized water. A separate 6.8% solution of sodium carbonate in water was also prepared by adding 297 g of sodium carbonate to 4.37 L of deionized water. Using a clean addition funnel, the sodium carbonate solution was then slowly added with stirring to the suspension of the starting material, to create a brown-colored solution.

In preparation for the reaction step, the phosgene solution was warmed from $-45°$ C. to $-15°$ C. and the mixture of the starting material and the sodium carbonate was cooled to 10° C. The phosgene solution was then added over approximately 1.5 hours with stirring to the brown solution. The reaction mixture was stirred overnight allowing the desired intermediate-A (formula II):

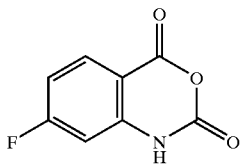

II to precipitate out. A sample was removed for NMR assessment and the precipitate was filtered on a 4 L sintered glass funnel. The filtrate was washed with 2×500 ml aliquots of cold deionized water and dried under a vacuum at approximately 50° C. for 16 hours.

A 93.4% lot yield of 435 g of intermediate-A (formula II) was obtained. This procedure was repeated three more times, starting with approximately 400 g of starting material each time. Lot yields of 448 g (94.5%), 449 g (95.9%), and 459 g (96.8%) were obtained.

ii. Step II

In a 22 L oven dried glass reactor equipped with a reflex condenser, addition funnel and temperature recorder, 11.40 L of anhydrous tetrahydrofuran (THF) were added under nitrogen. To this reactor were also added 409 g of 60% sodium hydride in oil. Eight approximately equal portions of intermediate-A (formula II) were then added to the reactor, totaling 883 g altogether. As this reaction is exothermic, care was taken to avoid excessive heat and bubbling. Final temperature was 40° C., with a maximum observed temperature of 41° C. The reaction mixture was stirred until hydrogen gas evolution ceased.

To the reaction mixture was then slowly added 575 ml (766.4 g) of dimethyl sulfate, keeping the temperature below 50° C. Upon completion, the reaction mixture was stirred at 50° C. for 3 hours with the reflux condenser on. A sample was removed for NMR assessment, and the heat was turned off before stirring overnight.

In the morning, the stirring was stopped and the clear liquid on top was siphoned off. This liquid was filtered using a 2–3 inch thick Celite pad in a 2 L sintered glass funnel. The residue cake was kept covered to minimize contact with atmospheric moisture. The residue was collected and washed with 4 aliquots of anhydrous THF. The filtrate and the washings were evaporated to dryness using a rotary evaporator and the residue obtained was dried under vacuum at approximately 36–38° C. overnight. A sample was removed for NMR assessment of the amount of unreacted dimethyl sulfate present. The dried residue was then added to 1600 ml of a 1:3 toluene:hexane mixture and vigorously stirred. This mixture was then filtered and washed with 2×700 ml washings of 1:3 toluene:hexane mixture. A reference sample was removed for NMR assessment and the residue was dried at 51–50° C. under vacuum for 36 hours.

This batch yielded 871 g of intermediate-B (formula III):

III

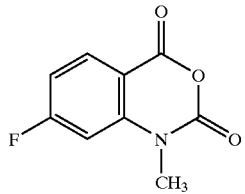

for a lot yield of 91.6%. Another 907.1 g of intermediate-A was subjected to the procedure of step II, in which the amounts of reactants and solvents was proportionately adjusted with a yield of 850 g (87%).

iii. Step III

In an oven dried 12 L glass reactor equipped with a stirrer, temperature recorder and addition funnel, 2550 ml of anhydrous toluene was added under nitrogen. Then 236 g of 60% sodium hydride in oil was added, all at room temperature. The reaction mixture was heated with continuous stirring to 75° C. using a heating mantel. Then 1.59 L of anhydrous dimethyl sulfoxide (DMSO) were added slowly and carefully over 45 minutes taking care to avoid excessive bubbling. The reaction mixture was stirred for one hour at 70–72° C. until clear and hydrogen gas evolution ceased. The heating mantel was turned off and a water bath was used to cool the reaction mixture to 30° C.

To this mixture, 538.2 g of dry intermediate-B (formula III) was added slowly in portions, keeping the temperature no higher than 35° C. Then 1.9 L of anhydrous DMSO was added, again keeping the temperature no higher than 35° C. The reaction mixture was stirred under nitrogen for one hour, allowing the mixture to cool to 26°. The reaction mixture was then quenched slowly and carefully with 320 ml of methanol. The resulting suspension was then added slowly and with vigorous stirring to a 22 L reaction vessel containing 12.760 L of diethyl ether.

After stirring was stopped, the upper ether layer was siphoned off and the brown oil lower layer was washed with 520 ml of fresh ether. The oily yellow residue was triturated with 2600 ml of deionized water until a yellow precipitate formed. This precipitate was filtered using a 2 L sintered glass funnel and the solid residue was washed with three aliquots of 130 ml cold deionized water. A reference sample was taken to assess the residue. The residue was dried under vacuum at 50–53° C. for 23 hours.

This procedure produced 243 g of intermediate C (formula IV):

IV

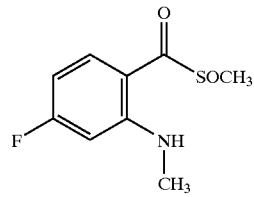

which represents a 38.4% yield. Two other batches of intermediate-B were treated according to this Step III procedure, with proportionate adjustments to the amounts of reactants and solvents. The first additional batch of 538.2 g intermediate-B produced a 192 g (30.4%) yield, and the second additional batch of 87.38 g of internediate-B produced a yield of 42 g (40.9%).

iv. Step IV

In a 12 L oven dry glass reactor equipped with a stirrer, temperature recorder and addition funnel which has been dried by nitrogen flow for 30 minutes the following chemicals were charged: 7.990 L of triethyl orthoformate; 696 g of intermediate-C; 324 ml of piperdine; and 296 ml of acetic acid. The reaction mixture was heated under nitrogen to reflux at approximately 105° C. for 2 hours. A sample was removed to assess the progress of the reaction step by NNR.

Using a water bath, the reaction mixture was then cooled to room temperature and stirred for 30 minutes. The final product precipitated out and was collected by filtration on a 4 L sintered glass funnel. The residue was washed with 3×700 ml aliquots of diethyl ether, and a sample was removed for NMR assessment. The residue was dried under vacuum at 50–51° C. for 17 hours. A sample of the dried flosequinan product (formula V):

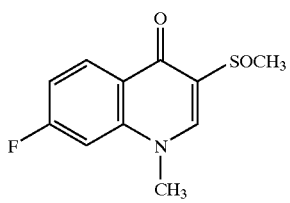

was removed for NMR assessment. 547 g (75.3%) yield of flosequinan was obtained (an additional 47 g of product was scraped from the bottom of the sintered glass filter but was not included in this total yield calculation).

EXAMPLE 3

In this example, carboxyflosequinan was subjected to biochemical enzyme assays and radioligand binding assays to determine its percent inhibition of a variety of enzyme activities. Tamaoki and Nakano "Potent and specific inhibitors of protein kinase C of microbial origin" *Biotechnology* 8:732 (1990); Wilkinson et al. "Isoenzyme specificity of bisindolymaleimides, selective inhibitors of protein kinase C" *Biochem. J.* 294:335 (1993); Tamaki et al. "Staurosporine, a potent inhibitor of phospholipid/Ca++ dependent protein kinase" *Biochem. Biophys. Res. Comm*, 135:397 (1986). A brief summary of the conditions for each assay is provided below:

Protein Serine/Threonine Kinase PKCα: Human recombinant enzyme from Sf9 insect cells was used in the assay. The substrate was 200 µg/ml histone. The reaction was incubated 10 mins at 25° C. in 20 mM Hepes, 10 mM $MgCl_2$, 0.1 mM $CaCl_2$. [$^{32}$P]histone was quantitated.

Protein Serine/Threonine Kinase PKC, non-selective: The enzyme was obtained from rat brain and the substrate was 370 µg/ml histone. The reaction was pre-incubated 5 min at 25° C., followed by a 15 min incubation at 25° C. in a buffer of 20 mM Tris-HCl, 10 mM $MgCl_2.H_0$ and 0.1 mM $CaCl_2.2H_0$, pH 7.4. [$^{32}$P]histone was quantitated.

FIG. 3 projects data for carboxyflosequinan in the assays described above. In these protein kinase assays, carboxyflosequinan was used in varying concentrations (in 1% DMSO as the vehicle). For the protein serine/threonine kinase (PKC, non-selective), carboxyflosequinan was tested at a concentrations of 100 µM, 300 µM, and 1000 µM.

Significant (e.g., greater than 50%) inhibition was observed at all three concentrations of carboxyflosequinan. (See, FIG. 3).

All publications and patents mentioned in the above specification are herein incorporated by reference. Various modifications and variations of the described invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A composition comprising 3-carboxymethylsulfinyl-7-fluoro-3-methyl-4-quinolone having the corresponding structure:

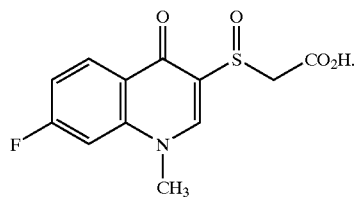

2. A pharmaceutically acceptable formulation comprising said composition of claim 1.

3. The formulation of claim 2, wherein said formulation is a salt, wherein said salt is capable of administration to a subject.

4. The formulation of claim 2 further comprising a binder.

5. The formulation of claim 2 further comprising a filler.

6. The formulation of claim 2 further comprising a carrier.

7. The formulation of claim 2 further comprising a preservative.

8. The formulation of claim 2 further comprising a stabilizing agent.

9. The formulation of claim 2 further comprising an emulsifier.

10. The formulation of claim 2 further comprising a buffer.

11. The formulation of claim 2 further comprising an excipient.

* * * * *